Figure 1:
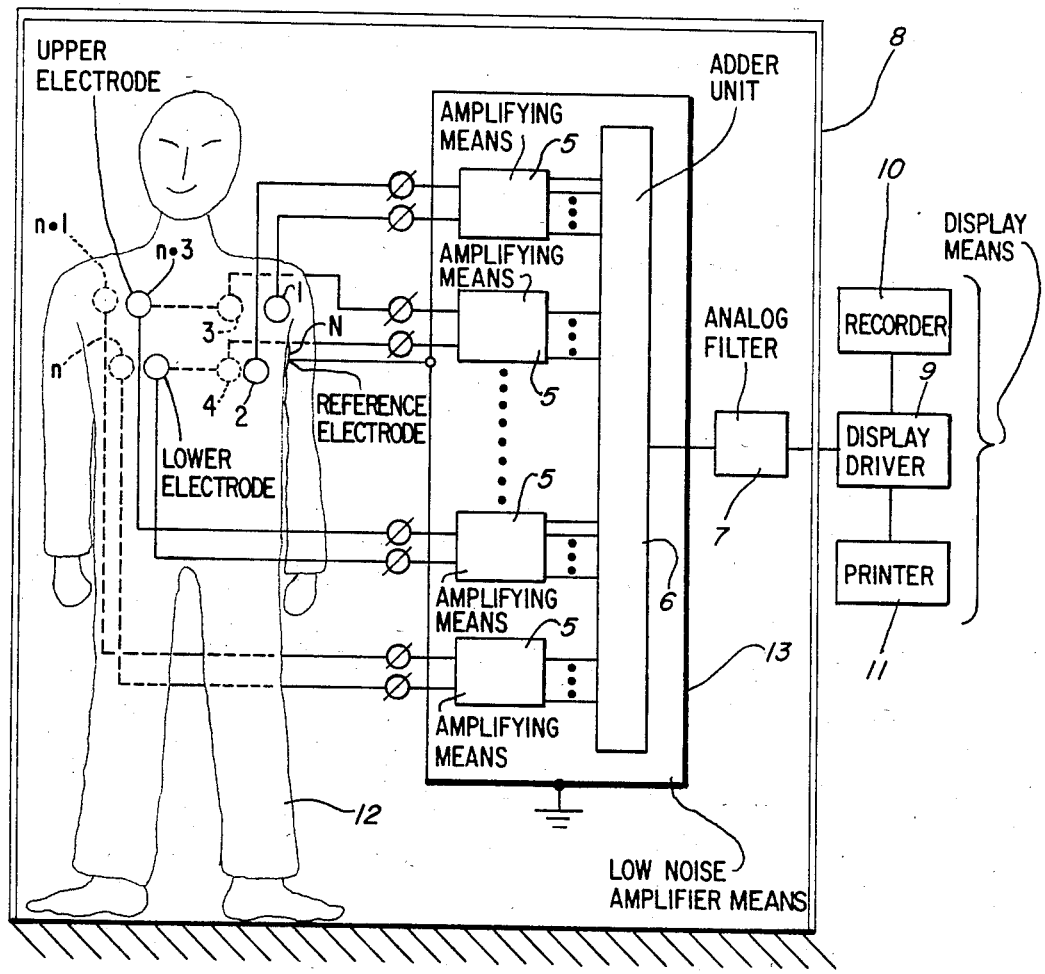

United States Patent [19]

Kepski et al.

[11] Patent Number: 4,593,702
[45] Date of Patent: Jun. 10, 1986

[54] MEASURING SYSTEM FOR THE ELECTRICAL ACTIVITY OF THE HEART CONDUCTING SYSTEM ON THE BEAT-TO-BEAT BASIS BY A NONINVASIVE METHOD

[75] Inventors: Roman Kepski; Franciszek Walczak; Zbigniew Plucinski; Adam Piatkowski, all of Warsaw, Poland

[73] Assignee: Osrodek Badawczo-Rozwojowy Techniki Medycznej "Ormed", Warsaw, Poland

[21] Appl. No.: 434,903

[22] Filed: Oct. 18, 1982

[30] Foreign Application Priority Data

Oct. 22, 1981 [PL] Poland .................. 233539[U]

[51] Int. Cl.⁴ ............................... A61B 5/04
[52] U.S. Cl. ...................... 128/696; 128/699
[58] Field of Search ................ 128/696–697, 128/699, 700, 709

[56] References Cited

U.S. PATENT DOCUMENTS

| | | | |
|---|---|---|---|
| 3,547,104 | 12/1970 | Buffington | 128/696 |
| 3,878,832 | 4/1975 | Tickner et al. | 128/696 |
| 4,194,511 | 5/1980 | Feldman | 128/696 |
| 4,318,412 | 5/1982 | Stanly et al. | 128/696 |

FOREIGN PATENT DOCUMENTS

| | | | |
|---|---|---|---|
| 2758347 | 6/1978 | Fed. Rep. of Germany | 128/696 |
| 1379656 | 1/1975 | United Kingdom | 128/696 |

OTHER PUBLICATIONS

Wajszczuk et al.; "Noninvasive Recording of His-Purkinje Activity in Man by QRS-Triggered Signal Avging"; Circulation, vol. 58, No. 1, 7–1978, pp. 95–102.
Walczak, F., Kepski, R., Plucinski, Z., Platkowski, A.; "Noninvasive Method of His-Purkinje System (HPS) Activation Measurement Without Averaging"; Kard. Pol., 1980 vol. XXIII, No. 7, pp. 625–629.
Kepski, R., Plucinski, Z., Walczak, F., Platkowski, A.; "His-Purkinje (HPS) System Activation Measurement from the Chest Surface in Consecutive Heart Evolutions", Post. Fiz. Med., 1980, vol. XV, No. 4, pp. 185–193.
Stopczyk, M. J., Walczak, F., Kepski, R., Plucinski, Z., Peczalski, K.; "The History of Noninvasive His-Bundling Recording: From Averaging to Continuous Method", Signal Averaging Technique in Clinical Cardiology, Int. Symp. F. K. Schattauer Verlag-Stuttgart-N.Y., 1981, pp. 283–289.

Primary Examiner—Edward M. Coven
Assistant Examiner—Angela D. Sykes
Attorney, Agent, or Firm—Ladas & Parry

[57] ABSTRACT

The subject of the invention is a measuring system of the heart-conduction system on the beat-to-beat basis by a noninvasive method. It relates to electrophysiological measurements, especially the measurement of very weak voltages of the surface of patient's chest, representing the activation of a specialistic heart-conduction system. The measuring system according to the invention consists of a large number of pairs of measuring electrodes situated preferably along the line of geometrical projections of the heart-conduction system onto the surface of patient's chest and these pairs of electrodes co-operate with a large number of parallely connected amplifying elements, forming together with them parallel amplifying tracks wherefrom summed up voltage is characterized by a signal increase proportionally to the number of the said tracks and by noise increased proportionally to the square root from the number of the said tracks—due to which the signal-to-noise ratio is improved and then the signal is fed to analog and/or digital filtration.

7 Claims, 2 Drawing Figures

MEASURING SYSTEM FOR THE ELECTRICAL ACTIVITY OF THE HEART CONDUCTING SYSTEM ON THE BEAT-TO-BEAT BASIS BY A NONINVASIVE METHOD

The invention relates to electrophysical measurements, and especially the measurement of very weak voltages from the surface of the chest representing the activitation of the specialized His-Purkinje heart conducting system of the heart.

The hitherto routinely applied method of the measurement of the heart conducting system activation consisted of introducing an electrode into the patient's heart under radiological control and after skillful placing in a direct vicinity thereof, His-bundle measuring of the electrical potentials acting on this electrode. The so-called "His Bundle Electrogram" thus obtained, as a method of evalution of the stimulation-conduction system enables, indeed, a direct measurement of activitation of internodal pathways, the AV node and the His-Purkinje system—is not devoid, however, of a considerable inconvenience which is the result of invasive action (introduction of a catheter with an electrode into the heart).

The second known method of the conduction system activation measurement consists in measurement of voltages from the chest surface by the method of so-called digital averaging. This method employs the periodic character of the measured signal appearing as a rule at each systole. The measured signal (of a small amplitude), except for certain pathologic situations, appears always at the same time distance from the "R" wave of an electrocardiogram or from the stimulation signal (if stimulation is performed).

The averaging method utilizes the above mentioned constant time relation between the reference signal (e.g. "R" wave) and the signal measured in such a way that starting from the moment of the arrival of a succeeding "R" wave (called the synchronizing signal) the course of voltage over a time segment sufficiently large to include the measuring signal is recorded in succeeding memory cells of an averaging computer. Incidental noise (signals not associated with the synchronizing signal) adopt different values in succeeding cycles and their average instantaneous value at a sufficiently big number of repetitions aims at zero.

Meanwhile the measuring signal arriving, in general, in an identical time displacement with respect to the synchronizing signal in succeeding repetitions is summed up adopting in a corresponding memory cell of the computer a higher and higher value. The basic dependence of averaging is presented by the formula:

$$\sum_{i=1}^{m} \frac{Si}{Ni} = \sqrt{m} \cdot \frac{S}{N}$$

where:
S—measuring signal (rms value)
N—noise (rms value)
m—number of repetitions This results from the fact that if we want, for example, to improve the signal-to-noise ratio by 10 times, 100 repetitions should be performed.

In the known methods of this type of measurements two measuring electrodes were used (apart from the third reference electrode). Application places of measuring electrodes depending on the research centre of the clinic were very differently assumed. There is a method known in which two electrodes are situated, for example: along the long axis of the heart, one electrode being placed in place V3 (on the chest) and the other one opposite it but on the back, or both electrodes, are placed in a patient's armpits on the same lateral line. These electrodes were connected with a symmetrical amplifier, forming a single measuring track. The output of the amplifier was connected to a computer averaging voltages from succeeding evolutions of the heart. The above method has an advantage in relation to the His-bundle electrogram because of its noninvasiveness. On the other hand, it has inconveniences whereof the most important one consists in weakening or not recording nonperiodic information appearing in certain diseases (transient arrhythmia).

The most preferable solution would be a system enabling both noninvasive measurement and without averaging from many heart evolutions—that is, combining advantages of both the above described measurement methods.

The essence of the present invention is a measuring system consisting of a large number of measuring tracks, whereby each of these tracks consists of one pair of electrodes connected with one low-noise amplifying block which comprises a set of parallelly connected amplifiers. Outputs of these tracks are connected to an adder after which there is a system of analog filters and a computer enabling further digital filtration and output data display on peripheral equipment.

Each pair of electrodes consists of an upper electrode lying preferably opposite the upper part of the heart-conduction system and a lower electrode lying opposite the lower part of the heart-conduction system, thus, each pair of electrodes measures a potential proportional to the projection of the vector of activation wave voltage (agreeing approximately with the resultant direction of the spatial structure of the HPS system) onto the surface of patient's chest. Due to the large number of pairs of measuring electrodes the summed up signal has a relatively large amplitude independently of the spatial location of the heart-conduction system in the patient's body. The signal is amplified in parallel amplifying tracks and summed up arithmetically, whereby the noise and interferences of the measuring system, which accompany the signal, increase only proportionally to the square root from the number of summed up courses (according to the nature of phenomena of an incidental character and Gauss probability distribution). The measurement does not require the observance of the principle of periodicity of the signal and can relate to a single physical phenomenon (e.g. measurement of weak voltages from the stimulation-conduction system in a single heart beat). It also ensures preferable summing up projections of the vector of activation wave passing along the heart conduction system by a parallely connected multiplied measuring system, due to which considerable gain of independence of the amplitude of the measured signal from the individual spatial position of the heart in patient's chest is obtained.

Figure 2:
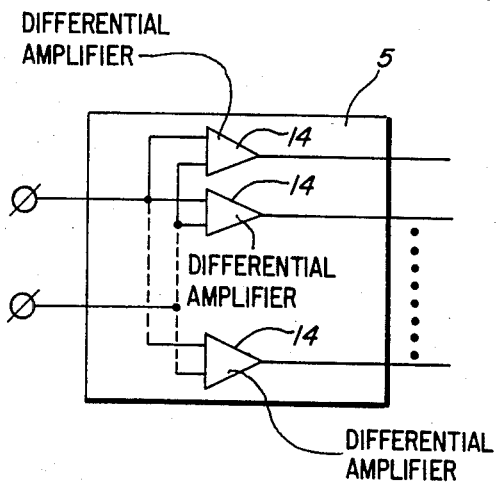

The subject of the invention is presented in an example of its realisation in a schematic diagram in which FIG. 1 which shows the measuring system of activation of the heart-conduction system by a noninvasive method with indication of patient's electrodes, and FIG. 2 shows a block of parallely connected amplifiers.

During measurement of a signal of the heart-conduction system by a noninvasive method on the beat-to-beat basis according to the invention, a patient 12 rests on his back in a supine position in a Faraday's cage 8. A reference electrode N is situated in the patient's armpits, an electrode 2 being the electrode replacing a set of lower electrodes is situated between places in which as a rule precordial electrodes are placed V2 and V3, the upper electrode is situated on the front of the patient on the first intercostal space on the left-hand side in half of the distance from the sternum to the left armpit, an upper electrode n-3 is situated on the front of the patient on the first intercostal space on the right-hand side in half of the distance from the sternum to the right armpit, and an upper electrode n-1 is situated on the back between the line of the spine and the line of the shoulder blade, at the same height as the electrode n-3. At such an arrangement of electrodes the heart-conduction system (and especially its main part along the segment His-bundle-Purkinje fibres), irrespective of a possible deflection of the direction of the heart axis in particular patients, will be in the fork of electrodes 1-2, (n-3)-2, (n-1)-2.

Components of activation voltages will be different for all directions of the arrangement of electrodes. If one of components is smaller (for the reason of the position of the heart), then the other one will be bigger so that their sum will in most cases have a sufficiently big value for detection of the signal.

The further part of the measuring system comprises three parallel measuring tracks, whereby each of these tracks beginning with a pair of electrodes (1-2), (n-3)-2 and (n-1)-2) is connected with a block 5 of several parallely connected amplifiers 14 whose outputs are connected with an adder 6 whose output is connected with the input of analog filters 7 whose output is connected with a computer 9 to which a recorder 10 an a digital printer 11 are connected. Parallel connection of amplifiers 14 and the block 5 enables improving the signal-to-noise ratio of these amplifiers, thus, blocks of amplifiers 5 and an adding system from a unit of a low-noise amplifier 13. The application of the combination of three pairs of measuring electrodes enables improving the ratio of the signal to thermal noise (of electrode-skin resistance) and to other interferences from the surrounding space.

The computer 9 is provided with programmes enabling further digital processing of signals, their recognition and control of the recorder and the printer.

What is claimed is:

1. A system for measuring electrical activity of a heart conduction system in a patient's body from excitation to excitation during a single beat of the heart by a noninvasive method, comprising:
   at least two parallel channels, each channel defining a measuring track having a pair of electrodes, an upper electrode of said pair adapted to be located on the body not lower than the auricle level of the heart and a lower electrode of said pair adapted to be located on the body no higher than the ventricle level of the heart, means electrically connecting the electrodes of each pair to an amplifying means for producing amplified signals from each pair of electrodes during a heart beat;
   an adder means coupled to said amplifying means for summing the amplified signals from said electrode pairs to produce a sum signal;
   a filtering means connected to said adder means for filtering the sum signal to produce a filtered signal;
   display means connected to said filtering means for displaying the filtered signal; and
   a reference electrode adapted for application to the body, the reference electrode being connected to a common ground for the electrode pairs of each of the measuring tracks.

2. The system of claim 1, in which each pair of electrodes is adapted to be positioned on the body so that a line connecting the upper electrode and the lower electrode of each electrode pair is parallel to the longitudinal axis of the heart.

3. The system of claim 1, in which the upper and lower electrode of each pair are adapted to be located on the body in a spatial pattern around the torso surface, whereby HIS-Purkinje system electrical activation potential is measured.

4. The system of claim 1, in which each amplifying means comprises several amplifiers electrically connected in parallel.

5. The system of claim 1, in which the upper and lower electrodes of the electrode pairs are located on a patient's chest and back along extended lines of geometrical projection of the conduction system of the heart onto the patient's torso surface.

6. The system of claim 5, in which the upper electrodes are adapted to be located at the level of the first intercostal space and the lower electrodes are adapted to be located at the level of the lower part of the HIS-Purkinje system.

7. The system of claim 6, in which the lower electrodes are located at a level close to the tip of the heart.

* * * * *